United States Patent
Maa et al.

(10) Patent No.: US 10,709,899 B1
(45) Date of Patent: Jul. 14, 2020

(54) CLAMPING CIRCADIAN LIGHTING APPARATUS

(71) Applicant: Aleddra Inc., Renton, WA (US)

(72) Inventors: Chia-Yiu Maa, Bellevue, WA (US); Chun-Te Yu, Bellevue, WA (US)

(73) Assignee: ALEDDRA INC., Renton, WA (US)

( * ) Notice: Subject to any disclaimer, the term of this patent is extended or adjusted under 35 U.S.C. 154(b) by 0 days.

(21) Appl. No.: 16/530,880

(22) Filed: Aug. 2, 2019

Related U.S. Application Data

(63) Continuation-in-part of application No. 16/235,058, filed on Dec. 28, 2018.

(51) Int. Cl.
| | |
|---|---|
| *H05B 47/10* | (2020.01) |
| *A61N 5/06* | (2006.01) |
| *A61M 21/02* | (2006.01) |
| *H05B 47/105* | (2020.01) |
| *A61M 21/00* | (2006.01) |

(52) U.S. Cl.
CPC ........... *A61N 5/0618* (2013.01); *A61M 21/02* (2013.01); *H05B 47/105* (2020.01); *A61M 2021/0044* (2013.01); *A61N 2005/0663* (2013.01)

(58) Field of Classification Search
None
See application file for complete search history.

(56) References Cited

U.S. PATENT DOCUMENTS 10,022,556 B1 * 7/2018 Holbert ................. A61M 21/02

* cited by examiner

*Primary Examiner* — Dedei K Hammond
(74) *Attorney, Agent, or Firm* — Han IP PLLC; Andy M. Han

(57) ABSTRACT

A circadian lighting apparatus includes a housing, two light sources, and a control logic. The first light source has a higher color temperature (e.g. 5000K) and the second light source has a lower color temperature (e.g., 1900K). The control logic can clamp operation color temperature to a mixed high color temperature (e.g., 4000K) and a mixed low color temperature (e.g., 2700K), and operate the apparatus according to a circadian schedule such that the mixed high color temperature is used for a daytime circadian state and the mixed low color temperature is used for a nighttime circadian state, and the color temperature of the apparatus is bound by the mixed high color temperature and the mixed low color temperature. This apparatus enables a personalizeable circadian light where each user can set his/her own circadian color temperature range.

6 Claims, 5 Drawing Sheets

| Target Color Temperature | Power Consumption Ratio of 1900K LED | Power Consumption Ratio of 5000K LED |
|---|---|---|
| 1900K | 100% | 0% |
| 2200K | 84% | 16% |
| 2700K | 68% | 32% |
| 3000K | 58% | 42% |
| 3500K | 44% | 56% |
| 4000K | 28% | 72% |
| 4500K | 12% | 88% |
| 5000K | 0% | 100% |

CLAMPING CIRCADIAN LIGHTING APPARATUS

CROSS REFERENCE TO RELATED PATENT APPLICATION

The present disclosure is a Continuation-in-Part (CIP) of U.S. patent application Ser. No. 16/235,058, filed on Dec. 28, 2018, the content of which is herein incorporated by reference in its entirety.

BACKGROUND

Technical Field

The present disclosure pertains to the field of lighting devices and, more specifically, proposes a circadian lighting apparatus.

Description of Related Art

It is well known that circadian rhythm affects the behavior of animals, including human. Studies have also shown circadian lighting which is a lighting device based on a circadian rhythm could improve the recovery of patients in hospital. A circadian lighting works this way: a blue-enriched light stimulates the awareness and the alert level of the human body, thus suitable for working hours; a blue-depleted light clams down the human body to a lower alert level, thus suitable for off-work hours. Moreover, it is identified that human's circadian response curve over light spectrum differs than human's visual response curve. The blue-enriched light may be implemented by using a light source with a high color temperature, e.g., 5000K. The blue-depleted light may be implemented by using a light source with a low color temperature, e.g., 1900K.

FIG. 1 shows the spectral power distribution (SPD) of typical 1900K and 5000K LED light sources. As it can be seen from the SPD curves, the 5000K LED light sources indeed provides strong blue light SPD and the 1900K LED light sources is rather blue-depleted. It is not uncommon to use the combination of 1900K and 5000K LED light sources for making circadian lighting apparatus. However, the use of 1900K LED light source introduces another question. While its light is blue-depleted, the 1900K LED light source generates an amber color light. Not only the amber color light has a color temperature much lower than the warm white color at 2700K, which is the most popular color temperature for residential lighting application, but also the amber color is not a suitable color for use as a reading light. Existing implementations of circadian light leave users no choice but to accept an amber light for nighttime with poor reading light quality. A better solution is to devise a circadian lighting apparatus that allows a user to set his/her own circadian color temperature range, such that for people that is less sensitive to blue-induced sleep problem can set his/her nighttime circadian color temperature higher to 2700K (rather than 1900K) for a more comfortable reading light color. The same can be said for the high circadian color temperature. While some people prefer 5000K, others may want a lower color temperature at 4000K or even 3500K. Such needs are not properly addressed by the existing circadian lighting systems.

SUMMARY

The present disclosure introduces a clamping circadian lighting apparatus that allows a user to set his/her own circadian light color temperature range.

In one aspect, the present disclosure comprises a housing, two light sources, and a control logic. The first light source may have a higher color temperature such as 5000K, and the second light source may have a lower color temperature such as 1900K. The control logic has a means to mix the color temperature of the first and the second light sources to produce a mixed high color temperature (e.g., 4000K). The control logic also has a means to mix the color temperature of the first and the second light sources to produce a mixed low color temperature (e.g. 2700K). The control logic may operate according to a circadian schedule to transition the light output of the present disclosure from the mixed high color temperature at a daytime circadian state to the mixed low color temperature at a nighttime circadian state, and back and forth. The daytime circadian state is not restricted to daytime hours. For example, for night shift workers, their daytime circadian state would align to their working hours, 9 pm to 5 am, in order to keep their biological system on a highly active state during the working hours.

In some embodiments, the total light output of the present disclosure may be a linear combination of the light output of the first and the second light sources, in terms of the power consumption of first light source and the second light source. In other words, given a fixed overall wattage consumption W, the power consumption of the present disclosure is represented as the following formula:

$$W = Y*W1 + (1-Y)*W2$$

Where Y in [0%, 100%] represents the power consumption percentage of the first light source, (1−Y) represents the power consumption percentage of the second light source, and W1 and W2 represent the maximum wattages of the first and the second light sources, respectively. In some embodiments, W1 equals to W2, that is, the maximum power consumption of first light source equals to the maximum power consumption of the second light source.

In some embodiments, where W1 equals to W2 (both equal to W), the control logic of the present disclosure operates the circadian state transition according to a circadian schedule through a smooth (continuous) color-tuning between the mixed high color temperature and the mixed low color temperature by adjusting the power consumptions of first light source and the second light source. For example, the mixed high color temperature may be achieved at $$Y1*W + (1-Y1)*W \text{ at a fixed percentage } Y1,$$

and the mixed low color temperature may be achieved at $$Y2*W + (1-Y2)*W \text{ at a fixed percentage } Y2,$$

Then circadian state transition of the present disclosure can be represented as $$Y3*(Y1*W+(1-Y1)*W)+(1-Y3)*(Y2*W+(1-Y2)*W) = (Y3*Y1+(1-Y3)*Y2)*W+((Y3*(1-Y1))+(1-Y3)*(1-Y2)))*W,$$

where, $(Y3*Y1+(1-Y3)*Y2)*W$ represents the power consumption of the first light source, and $((Y3*(1-Y1))+(1-Y3)*(1-Y2)))*W$ represents the power consumption of the second light source, and that $$(Y3*Y1+(1-Y3)*Y2)+((Y3*(1-Y1))+(1-Y3)*(1-Y2))) = 1.$$

The continuous color-tuning mentioned above may require a rather complicate design of the control logic. In some cases, a simplified control logic that approximate the continuously color-tuning of the apparatus may suffice. Therefore, in some embodiments, the smooth (continuous)

circadian state transition according to a circadian schedule is approximated by a discrete color-tuning with a fixed number of linear combinations of the first and the second light sources.

Giving the end user a means for setting the mixed high color temperature and the mixed low color provides a great flexibility. However, for an average user, it would be difficult for the user to know which the right color temperature is. A better approach may be to offer the end the most popular choices. For example, for the mixed low color temperature, rather than offer any color temperature between 1900K and 3000K, it may be better to offer only four choices: 1900K (blue depleted), 2200K (low blue), 2700K (standard warm white), and 3000K (daylight warm white). Similarly, it suffices to offer four choices (3500K, 4000K, 4500K, and 5000K) for selecting the mixed high color temperature. Therefore, in some embodiments, the control logic of the present disclosure provides a set of mixed color temperatures of the first light source and the second light source to be selected from for setting the mixed high color temperature, and also provides a set of combined color temperatures of the first light source and the second light source to be selected from for setting the mixed low color temperature.

In another aspect, the present disclosure introduces a method operating at least two light sources each with a distinct color temperature. This method comprises setting a mixed high color temperature by mixing the color temperature of the at least two light sources, setting a mixed low color temperature by mixing the color temperature of the at least two light sources, and operating at least two light sources according to a circadian schedule. The combined color temperature range of the at least two light sources is bound by the mixed low color temperature and the mixed high color temperature.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

FIG. 4 shows a table with the power consumption ratios for 1900K and 5000K LED for achieving different mixed color temperatures.

FIG. 5 shows a discrete circadian schedule table with the power consumption ratios for 1900K and 5000K LED's, given the mixed low color temperature at 2700K and the mixed high color temperature at 5000K.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting apparatuses having different form factors.

EXAMPLE IMPLEMENTATIONS

Figure 1:
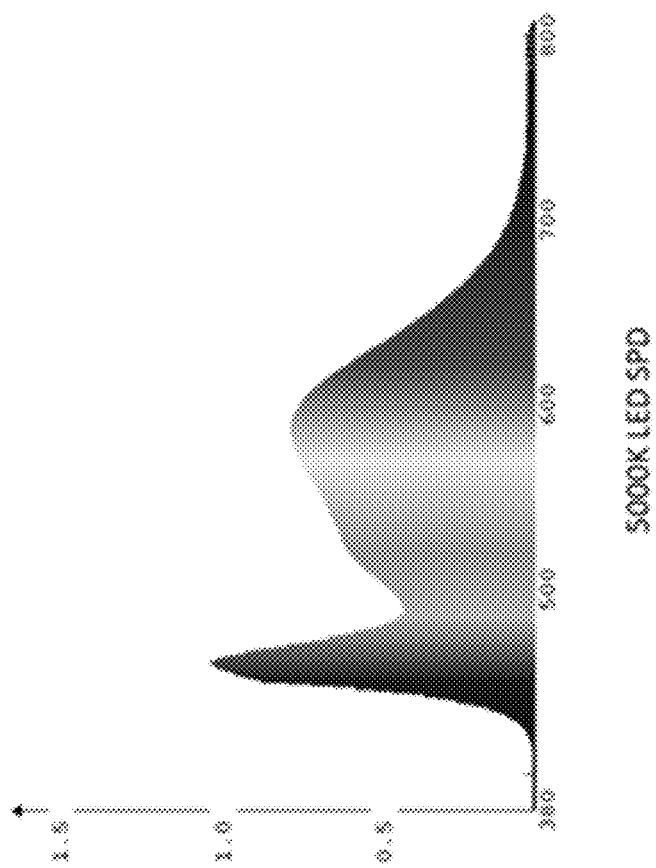
FIG. 1 shows the spectral power distribution of 1900K and 5000K LED light sources.
Figure 1:
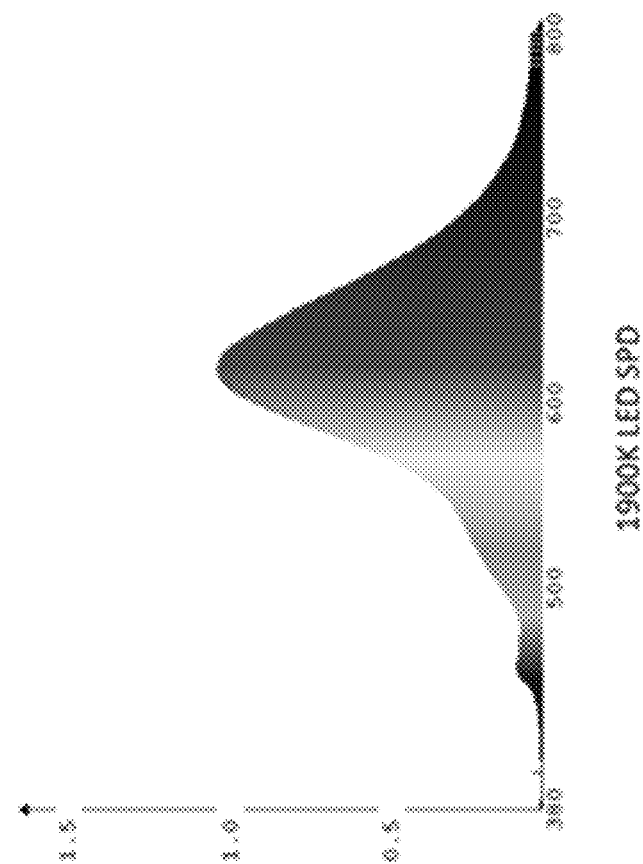
Figure 2:
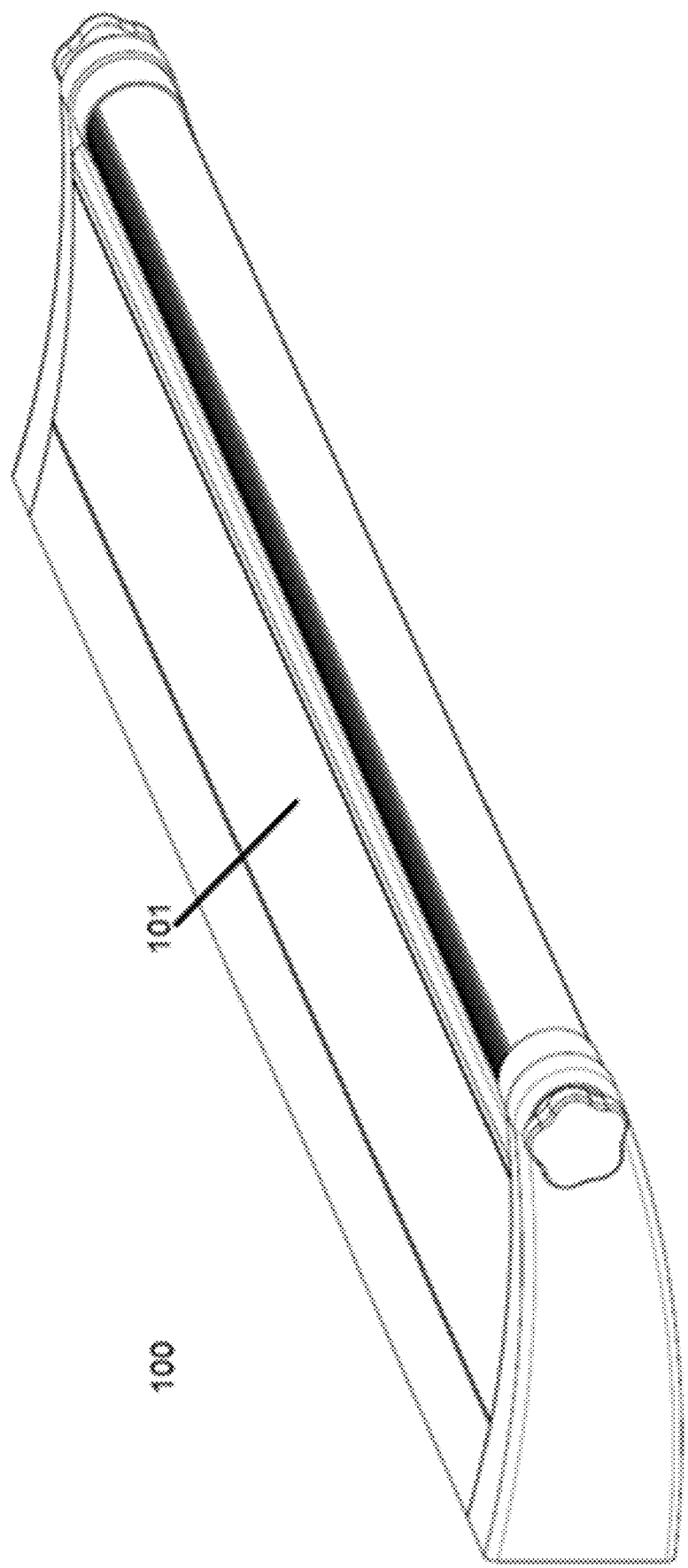
FIG. 2 schematically depicts the exterior diagram of a circadian lighting apparatus.
Figure 3:
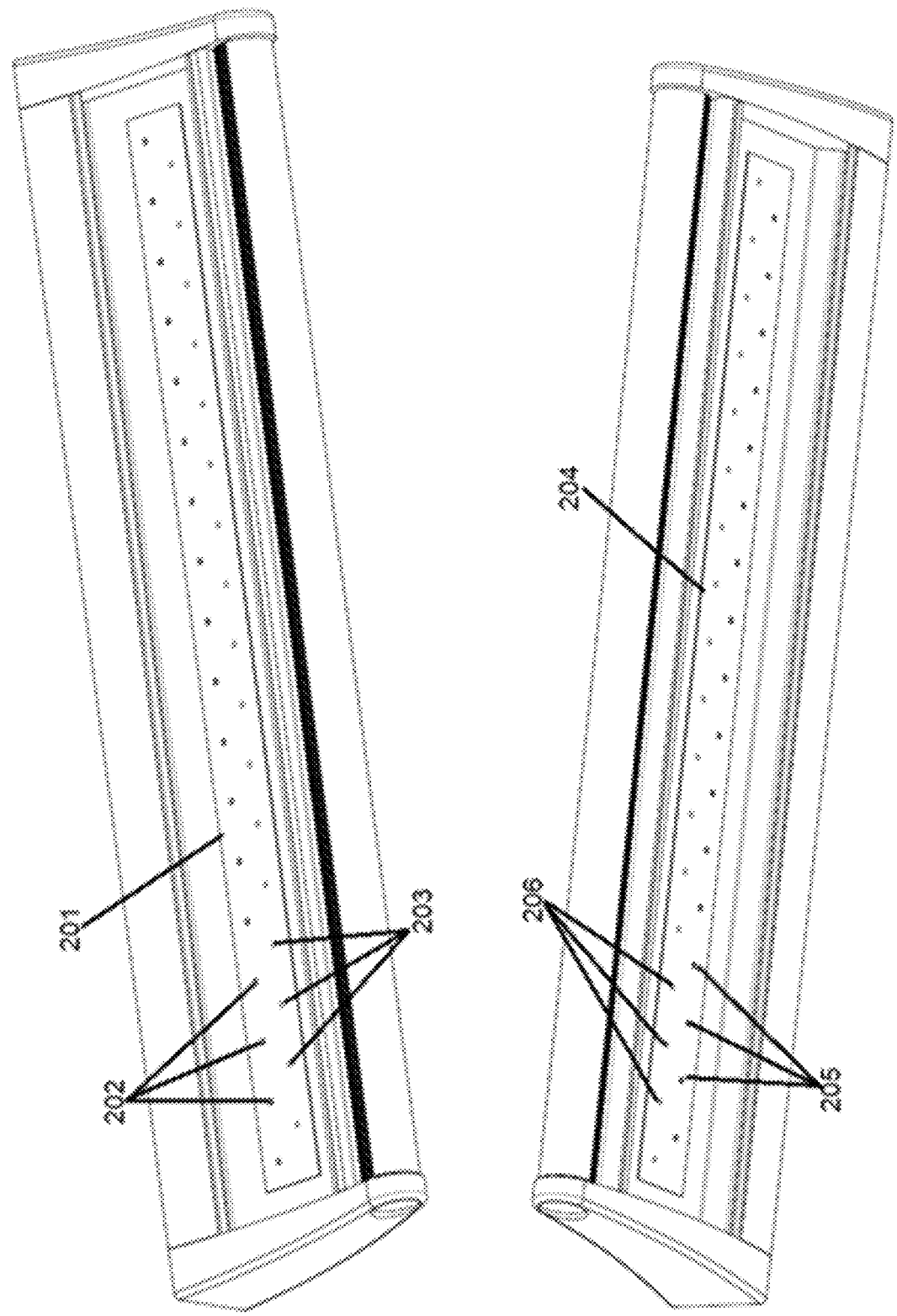
FIG. 3 schematically depicts an interior diagram of a circadian lighting apparatus using high color temperature LEDs and low color temperature LEDs.

The FIG. 2 is a circadian lighting apparatus 100 of the present disclosure in the form of an overbed lighting fixture. This apparatus has an up light 101 and a down light (not shown). The FIG. 3 shows the PCB boards of the up light and the down light. On the up light PCB board 201, there are two rows of LEDs, the blue-enriched LEDs 202 and the blue depleted LEDs 203. Similarly, on the down light PCB board 204, there are two rows of LEDS, the blue-enriched LEDs 205 and the blue depleted LED 206. All blue-enriched LEDs 202, 205 have a color temperature 5000K. All blue-depleted LEDs 203, 206 have a color temperature 1900K. For the up light or the down light, the total power consumption of its 5000K LED's equals the total power consumption of its 1900K LED's.

This example implementation uses a set of mixed low color temperatures, 1900K, 2200K, 2700K, and 3000K, and another set of mixed high color temperature, 3500K, 4000K, 4500K, and 5000K. The FIG. 4 shows a hypothetical model on the mixing of 1900K and 5000K LED's for achieving different mixed color temperatures.

Figure 5:
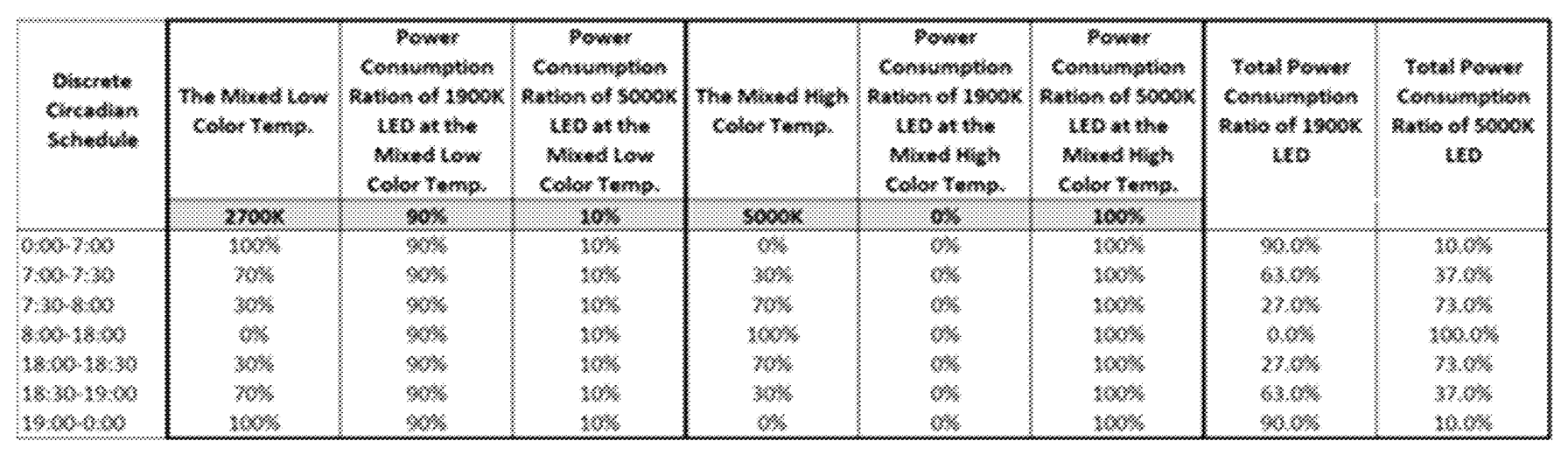

This example implementation also uses a discrete circadian schedule as shown in the first column of the table in FIG. 5. Each user may select a different mixed low color temperature and a different mixed high color temperature. The table shows the case when the mixed low temperature is 2700K and the mixed high temperature is 5000K. The total power consumption ratios of 1900K and 5000K LED's according to the discrete circadian schedule are calculated and shown in the last two columns of the table in FIG. 5. For example, during 7:00-7:30 am, the total power consumption ratio of 1900K LED is 63% and the total power consumption ratio of 5000K LED is 37%.

In some implementations, there may be more discrete circadian states, and even a continuous circadian state transition. The circadian schedule may be static or dynamically adjustable, for example, according to the season so there is a longer daytime circadian schedule in summer.

ADDITIONAL AND ALTERNATIVE IMPLEMENTATION NOTES

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A circadian lighting apparatus, comprising:
a housing;
at least two light sources comprising a first light source and a second light source; and
a control logic,
wherein:
the first light source has a first color temperature,
the second light source has a second color temperature lower than the first color temperature,
the control logic is configured to set a maximum operating color temperature, $CT_{max}$, to be lower than the first color temperature of the first light source, wherein $CT_{max}$ is achieved by mixing color temperatures of the first and the second light sources,
the control logic is also configured to set a minimum operating color temperature, $CT_{min}$, to be higher than the second color temperature of the second light source, wherein $CT_{min}$, is achieved by mixing the color temperatures of the first and the second light sources,
during operation in a circadian schedule, the control logic is configured to restrict a color temperature of the apparatus to be higher than $CT_{min}$ and lower than $CT_{max}$ throughout the circadian schedule,
the first light source comprises a blue-enriched light with greater than 18% spectral power distribution (SPD) in a wavelength range of 450~495 nm, and
the second light source comprises a blue-depleted light with less than 3% SPD in the wavelength range of 450~495 nm.

2. The circadian lighting apparatus of claim 1, wherein the total light output of the apparatus is a linear combination of a first light output of the first light source and a second light output of the second light source in terms of power consumptions of first light source and the second light source.

3. The circadian lighting apparatus of claim 2, wherein a maximum power consumption of first light source equals to a maximum power consumption of the second light source.

4. The circadian lighting apparatus of claim 3, wherein the control logic operates the circadian state transition according to the circadian schedule through a smooth and continuous color-tuning between $CT_{min}$ and $CT_{max}$ by adjusting the power consumptions of the first light source and the second light source.

5. The circadian lighting apparatus of claim 4, wherein the smooth and continuous color-tuning by the circadian state transition according to the circadian schedule is approximated by a discrete color-tuning with a fixed number of linear combinations of the first and the second light sources.

6. A method for operating at least two light sources each with a distinct color temperature, comprising:
setting a maximum operating color temperature, $CT_{max}$, to be lower than a first color temperature of a first light source of the at least two light sources, wherein $CT_{max}$ is achieved by mixing color temperatures of the first and the second light sources, the first light source comprising a blue-enriched light with greater than 18% spectral power distribution (SPD) in a wavelength range of 450~495 nm, the second light source comprising a blue-depleted light with less than 3% SPD in the wavelength range of 450~495 nm;
setting a minimum operating color temperature, $CT_{min}$, to be higher than a second color temperature of a second light source of the at least two light sources, wherein $CT_{min}$, is achieved by mixing the color temperatures of the first and the second light sources; and
restricting, during operation in a circadian schedule, a resultant color temperature to be higher than $CT_{min}$ and lower than $CT_{max}$ throughout the circadian schedule.

\* \* \* \* \*